(12) United States Patent
Hajarian et al.

(10) Patent No.: US 9,283,308 B2
(45) Date of Patent: *Mar. 15, 2016

(54) SUCTION TIP FOR SURGICAL INSTRUMENTS

(71) Applicants: Hamid Cyrus Hajarian, Fountain Valley, CA (US); Vahid Hamidi, Aliso Viejo, CA (US)

(72) Inventors: Hamid Cyrus Hajarian, Fountain Valley, CA (US); Vahid Hamidi, Aliso Viejo, CA (US)

(*) Notice: Subject to any disclaimer, the term of this patent is extended or adjusted under 35 U.S.C. 154(b) by 212 days.

This patent is subject to a terminal disclaimer.

(21) Appl. No.: 13/987,693

(22) Filed: Aug. 21, 2013

(65) Prior Publication Data

US 2015/0057609 A1 Feb. 26, 2015

(51) Int. Cl.
*A61B 17/00* (2006.01)
*A61M 1/00* (2006.01)

(52) U.S. Cl.
CPC .................................. *A61M 1/008* (2013.01)

(58) Field of Classification Search
USPC ................................ 600/200–246; 433/91, 93
See application file for complete search history.

(56) References Cited

U.S. PATENT DOCUMENTS

| 5,123,403 | A | 6/1992 | Lavyne |
| 7,226,413 | B2 | 6/2007 | McKinley |
| 8,545,401 | B2 * | 10/2013 | Hajarian et al. ............. 600/205 |
| 2007/0060793 | A1 * | 3/2007 | DeGould ..................... 600/201 |

* cited by examiner

*Primary Examiner* — Christopher Beccia
*Assistant Examiner* — Diana S Jones (57) ABSTRACT

A suction tip for a surgical instrument includes a hollow housing having a top flat wall and a bottom flat wall and including a proximal end and a distal end. The distal end has a widened tip portion that is wider than the proximal end. The distal end may have a plurality of suction ports located at its front, top, right side and left side of the widened tip portion. Furthermore a ledge portion may protrude outwardly past a terminal end of the top flat wall to provide a clear space between the suction ports and tissue for evacuation of fluid in the clear space. Furthermore, the ledge portion which protrude outwardly may have bended tip in desire degrees and shapes.

10 Claims, 15 Drawing Sheets

SUCTION TIP FOR SURGICAL INSTRUMENTS

This application claims priority to Provisional application Ser. No. 61/280,873 filed on Nov. 10, 2009, and non-provisional application Ser. No. 12/925,866 filed on Nov. 1, 2010, the entire contents of which is incorporated by reference herein.

FIELD OF THE INVENTION

The present invention relates to a surgical instrument with suctioning tip. More particularly the suctioning tip encompasses a wide range of evacuation.

BACKGROUND OF THE INVENTION

The importance of surgical retractors is well known in surgical procedures. A surgeon needs an exposure as best as possible while inflicting a minimum of trauma to the surrounding tissue. In some operations, such as oral surgery, a surgeon uses the tongue retractor to protect a patient's tongue from the medical procedure. An assistant surgeon or nurse performs continuous suctioning of fluid by placing a suction tube into the patient's mouth and performing the necessary evacuation to protect the patient from inhaling or swallowing fluids and scattered debris. Every time the assistant performs the evacuation process, the surgeon needs to halt the procedure and stop for few moments while the evacuation process takes place. To overcome this type of problem, there are few surgical retractors that have been designed with a suction tube mounted on the top of the tool to allow the surgeon to perform the evacuation process while performing the surgical procedure. Although the prior art devices eliminate some issues associated with this type of problem, there are limitations regarding suctioning of narrow range areas.

However, this invention overcomes the shortcomings and solves the problems associated with the prior art. This invention provides an improved suctioning tip for a wider range of evacuation that can be mounted on a conventional surgical retractor tip or it can be an integral part of a surgical retractor as a unitary piece.

SUMMARY OF THE INVENTION

It is an object of the present invention to provide an improved suctioning tip for a surgical instrument to cover a wider range of evacuation without creating any trauma to surrounding tissues. The suction tip apparatus comprises a hollow housing which has a proximal end and a distal end. At its distal end, the widened tip portion has a plurality of suction ports located at its front, on top, on its right side and also on left side. These suction ports along with the widened tip portion allow for suctioning of a wider range of an area. Furthermore a ledge portion provides a clear space between the suction ports and the tissue for means of evacuation and collection of fluid. An exit port near the proximal end is also provided for discharging fluid.

In preferred embodiment of present invention, the improved suction tip is an integral part of a surgical retractor. This unitary part can be designed in any desired shaped with respect to the shape of suctioning tip widen area.

It is also an object of this invention to mount or adapt a suctioning tip apparatus to any conventional surgical instrument that requires the wider range evacuation features.

It is yet another object of this invention to have the ledge portion that protrude outwardly to have bended tip in desired degrees and shapes.

Further objects and advantages of this invention will become apparent from consideration of the drawings and descriptions that follow.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE INVENTION

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figures 1, 2:
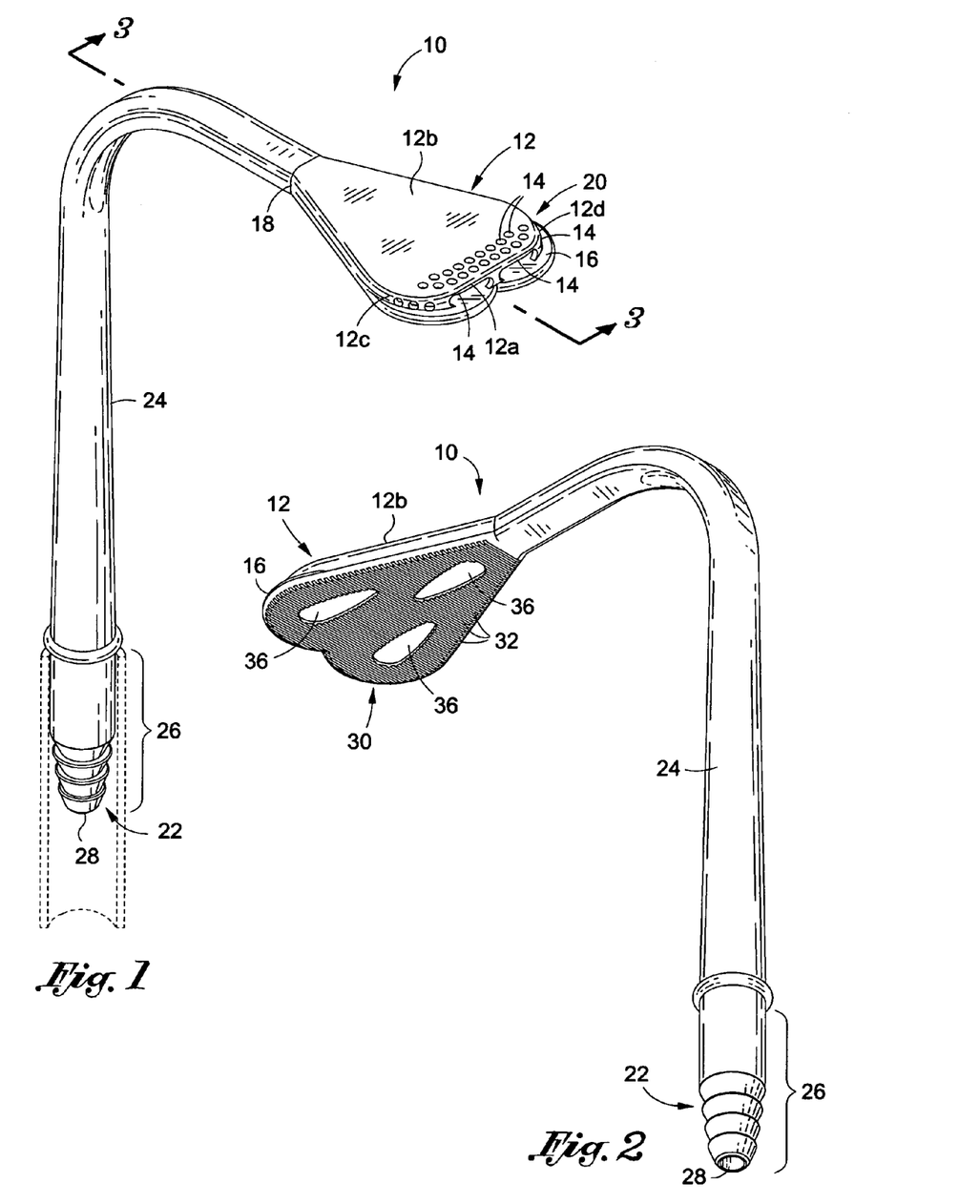
FIG. 1 is a top perspective view of a surgical retractor with suction tip showing the present invention of preferred embodiment.
FIG. 2 is a bottom perspective view of a surgical retractor as shown in FIG. 1.

FIG. 1 illustrates a preferred embodiment of a surgical retractor 10 with an improved suctioning tip. The retractor 10 is a right angle surgical tool that can be used in numerous surgical procedures such as oral surgery, vaginal surgery, abdominal surgery and etc. The surgical retractor 10 is made as a unitary part either in stainless steel material or in polymeric material such as polyetherimide or polyimide. One advantage of polymeric material is that it is non-conductive compared to stainless steel material and therefore is safer to use in some surgeries where thermal heat is involved and also they are disposable.

The surgical retractor 10 comprises a hollow housing that has a distal end 20 and a proximal end 22. At the distal end 20, the widened tip portion 12 has a plurality of suction ports 14 located at its front 12a, on top 12b, on its right side 12c and on the left side 12d. These suction ports 14 along with the widened tip portion allow for evacuation of a wider range of an area. Furthermore a ledge member 16 may extend out from its frontal side 12a of the widened tip portion for the purpose of abutting the tissue and providing a clear path between the suction ports 12 and the tissue for means of evacuation and collection of fluid in specified area "d". At the neck portion 18 of the suctioning tip 12, a narrow channel is formed with respect to its hollow housing for passage of any evacuation via its suction ports located at the widened tip portion 12. In this embodiment the tool body has a handle 24 near its proximal end 22 portion. The proximal end 22 also includes a vacuum hose connection port 26 for means of connecting a vacuum source to the surgical retractor 10. The connection port 26 include various sizes of connection to adapt different sizes of vacuum hose.

In general, the underside 30 of the surgical retractor 10 is flattened as shown in FIG. 2. In order to secure retractor 10 over body part in surgical procedures, serrated features 32 and recessed areas 36 have been added to the bottom of the retractor. These features eliminate any tool slippage over the body part. Also there may be suction ports added to the bottom to grab the body part if needed per specific tool operation.

Figure 3:
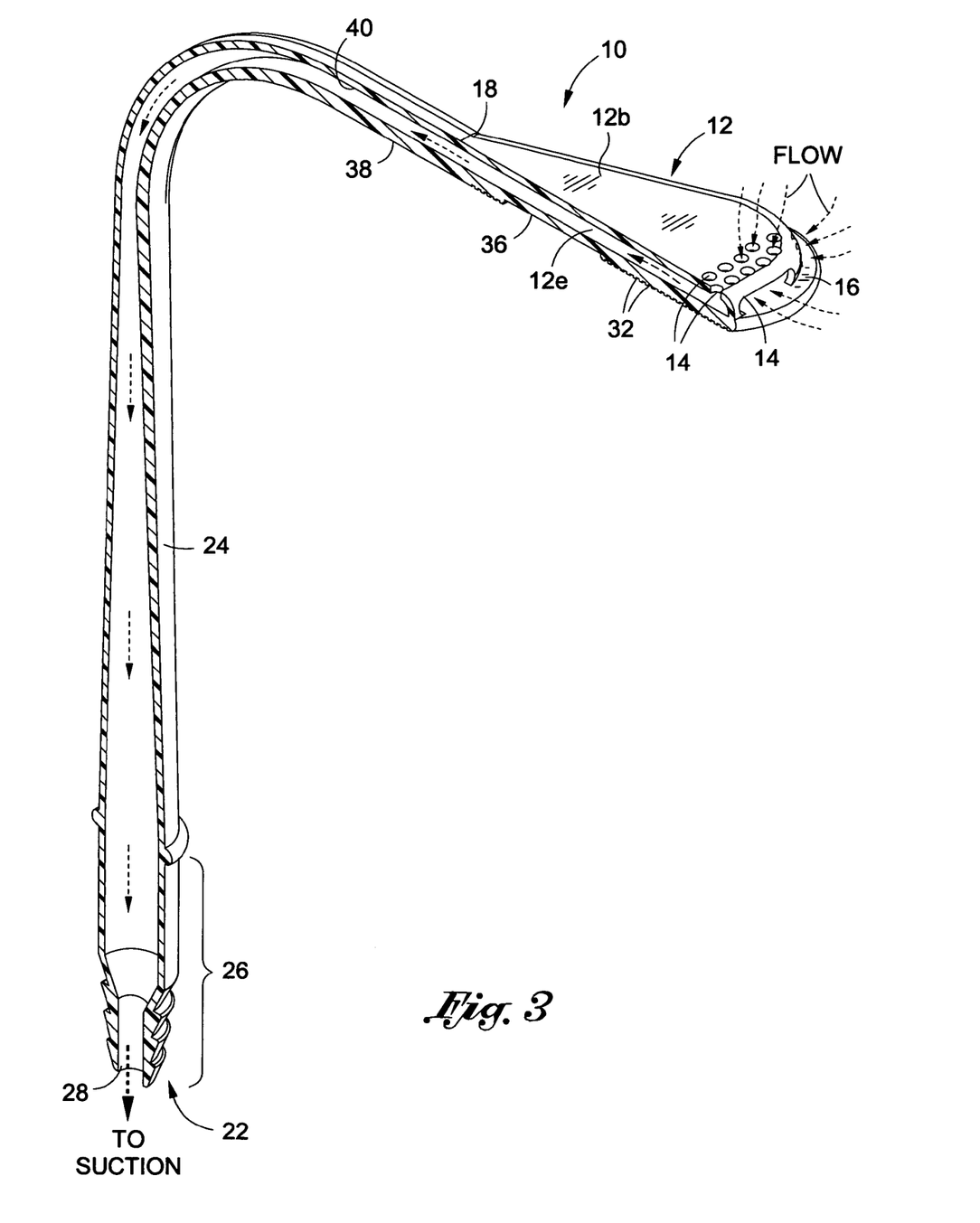
FIG. 3 is a section view taken along line 3-3 in FIG. 1.

In FIG. 3, a cross section of the unitary surgical retractor 10 is shown. When the vacuum flow enters into the tip chamber 12e via its suction ports 14, it is directed toward the narrow portion which is the neck area 18 and then via its lumen 40 directed to exit port 28 at the proximal end 22.

Figure 4:
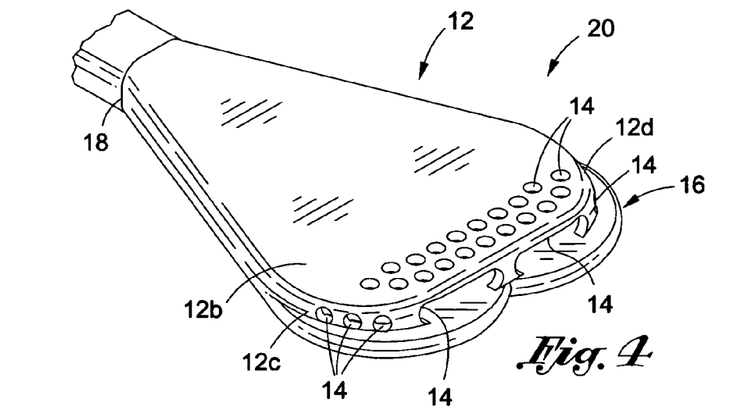
FIG. 4 is an enlarged view of the suction tip showing in FIG. 1
Figures 5, 6:
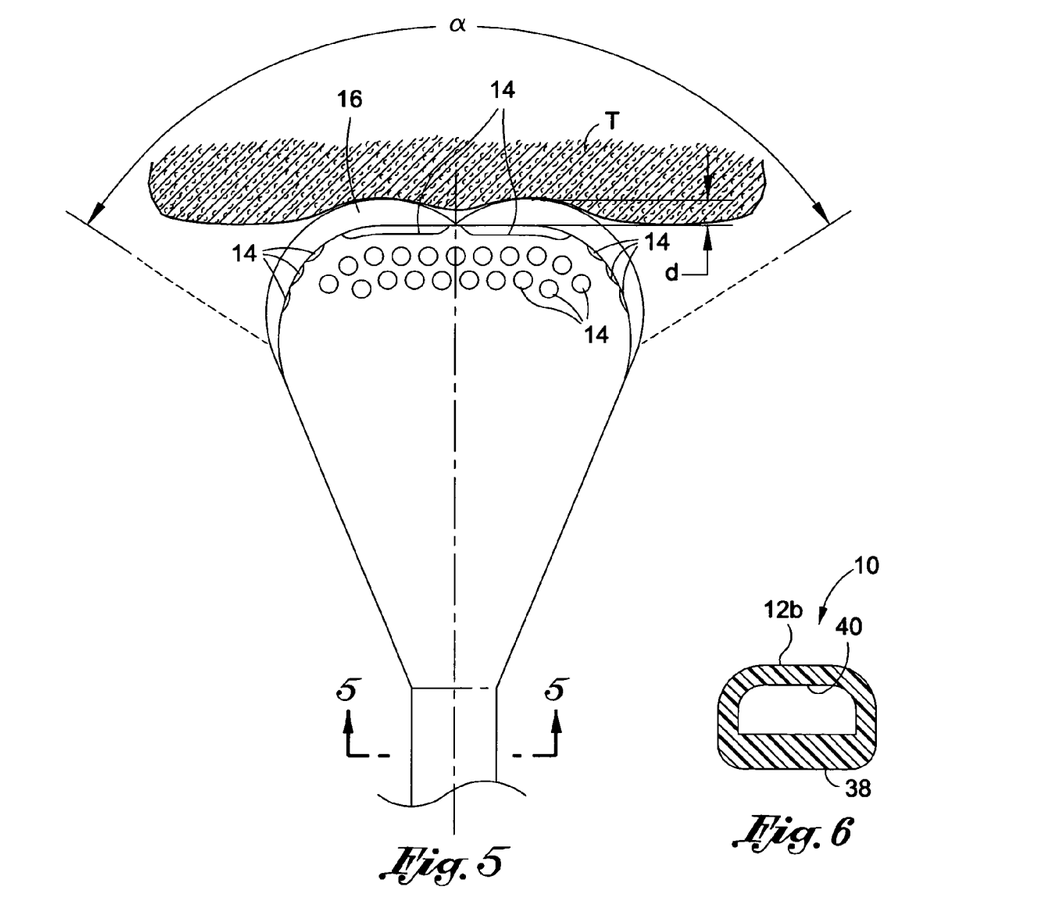
FIG. 5 is a top plan view of the suction tip as shown in FIG. 4.
FIG. 6 is a section view taken along line 6-6 in FIG. 5.

Referring to FIG. 4-5, enlarged views of the suction tip of the surgical tool are illustrated. The widened tip portion of the suction tip 12 has a wide range for collecting fluid or scattered particles as it is shown in operational angle α. Once the suction tip is abutting the tissue "T", the tip's ledge 16 provides a clear distance "d" between the tip and the tissue "T". Therefore a clearance path is provided for collecting fluid without direct contact of the suction ports to tissue. The advantages of this feature are to eliminate grabbing of the tissue by the frontal suction ports. Another advantage of having the multiple suction ports at the tip portion is to have continuous vacuum discharge regardless of whether some ports may be blocked. Once the vacuum is applied, the flow travels via the lumen 40 to the exit port at the distal end 22 as best shown in the cross section view FIG. 6.

Figure 7:
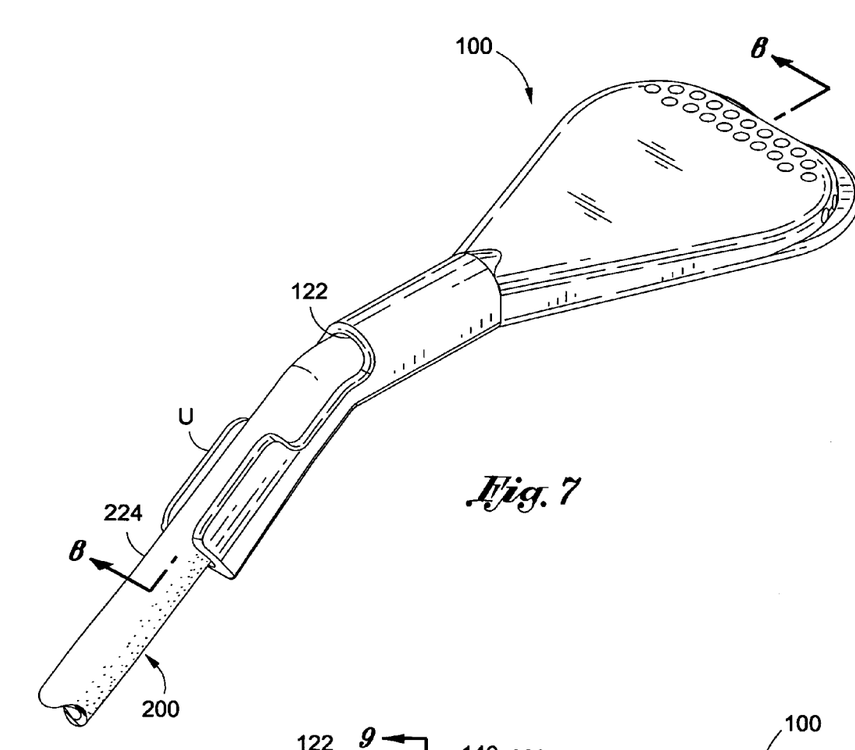
FIG. 7 is a rear perspective view of second embodiment of present invention.
Figures 8, 9:
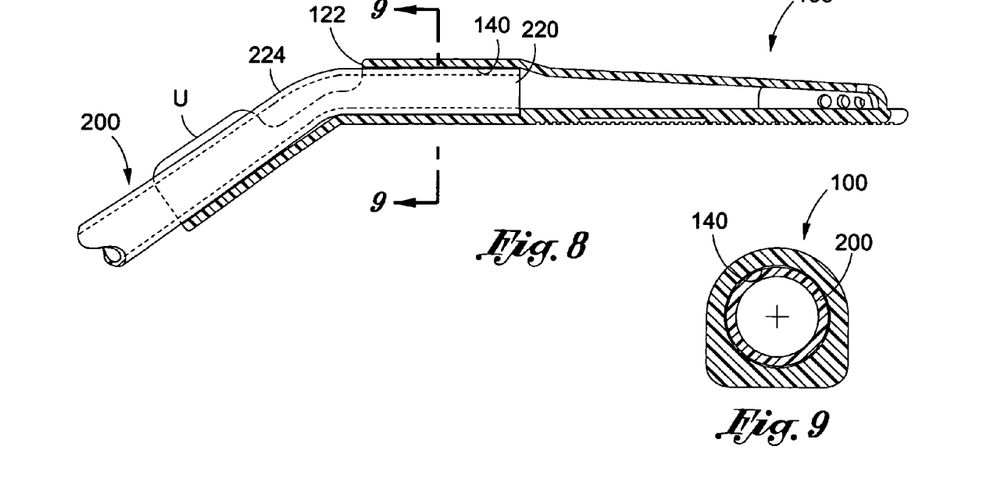
FIG. 8 is a section view taken along line 8-8 in FIG. 7.
FIG. 9 is a cross section view taken along line 9-9 in FIG. 8.

FIG. 7-9 illustrate a second embodiment of the improved suction tip 100 that can be adaptable and provide a wider range suctioning tip to an existing surgical tube 200. The tube's tip 220 snugly fits at the proximal end 122 of the suction tip 100. Once the tip 220 is secured into the distal end lumen 140, the tube's body 224 can be placed into the "U" shaped suction tip. The purpose of the "U" shape is to eliminate any tube 200 rotation and securely keep the suction tube in place with respect to the suction tip 100.

Figure 10:
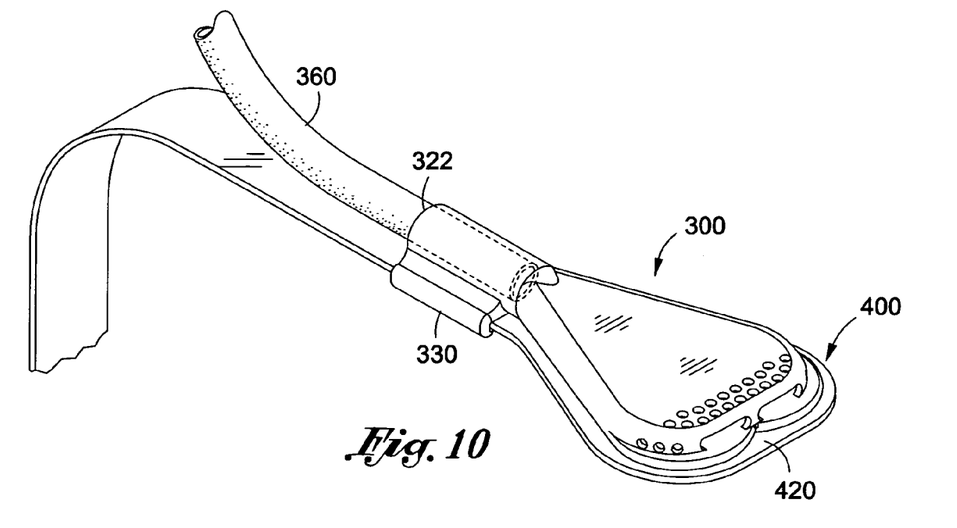
FIG. 10 is a top perspective view of third embodiment of present invention shown as assembled to a conventional surgical retractor.
Figure 11:
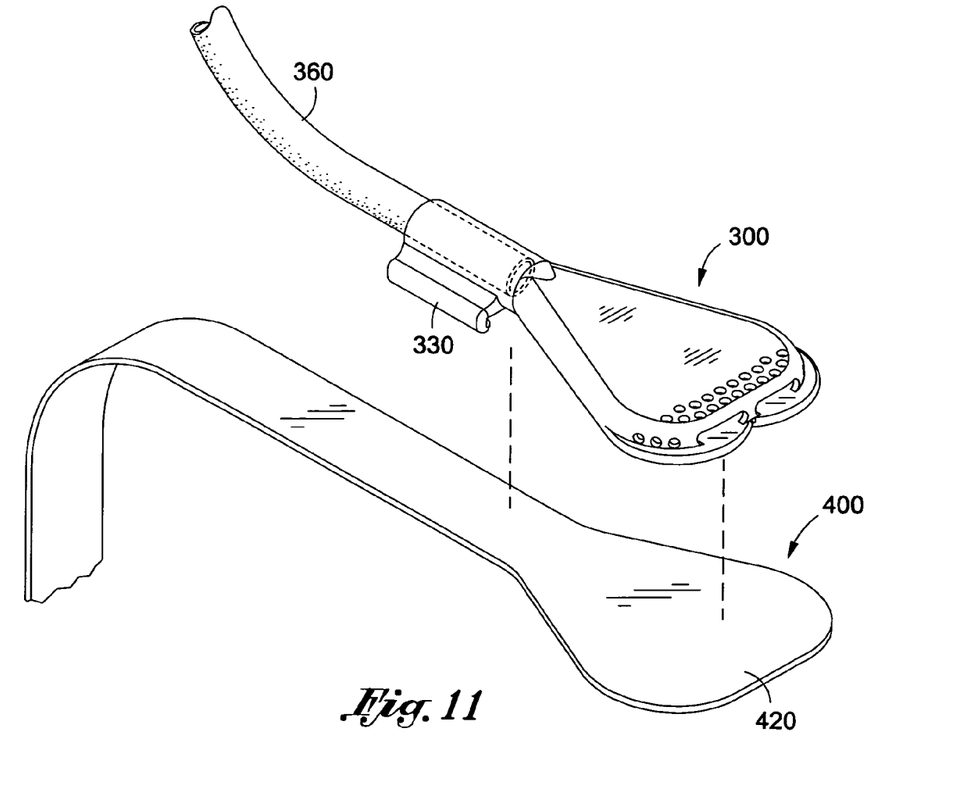
FIG. 11 is an exploded view of FIG. 10.

A third embodiment of the present invention is shown in FIG. 10-11. In this embodiment, the suction tip 300 is shown as a separated piece that is mountable to an existing surgical retractor 400 by placing it over the retractor tip 420. The suctioning tip apparatus 300 can be secured by means of attaching to the surgical retractor such as a clip 330, which is located at the bottom portion of the distal end 322 of the suctioning tip 300. Other means of attachment include adhesive or any fasteners between these two parts. Once the suction tip apparatus is placed over the surgical retractor, it can be connected to a vacuum tube 360 which provides a suction source to the tip portion.

Figure 12:
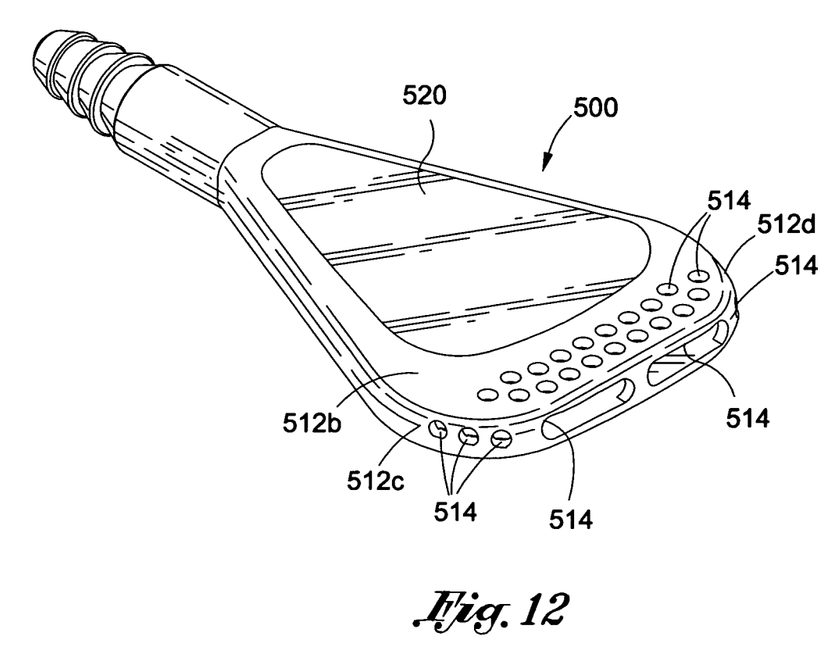
FIG. 12 is a perspective view of the an alternative embodiment of the suction tip.

A modified version of the suction tip apparatus 500 is shown in FIG. 12. In this embodiment, a mirror 520 has been added to the top surface 512b of the suction tip portion. In addition, at its proximal end, a connection port has been added which includes various sizes of connection to adapt different sizes of vacuum hose. Furthermore, the frontal ledge is eliminated in this embodiment.

Figure 12A:
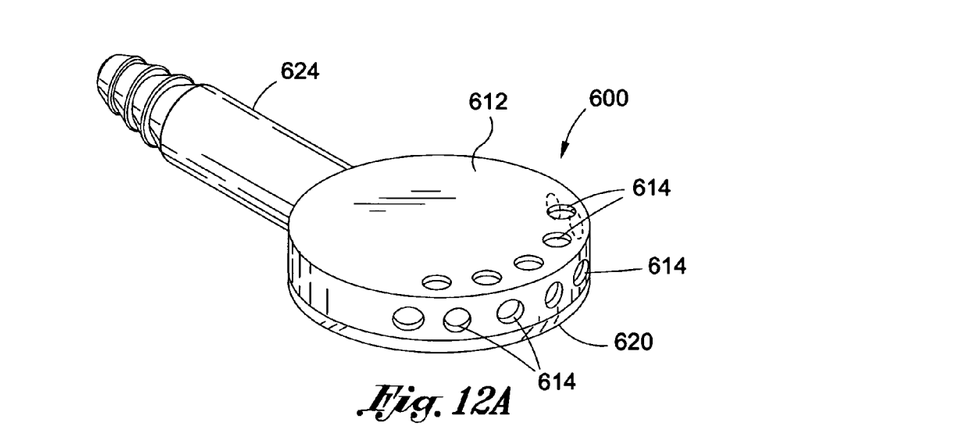
FIG. 12A is a bottom perspective view of a modified embodiment shown in FIG. 12 with added mirror.
Figure 12B:
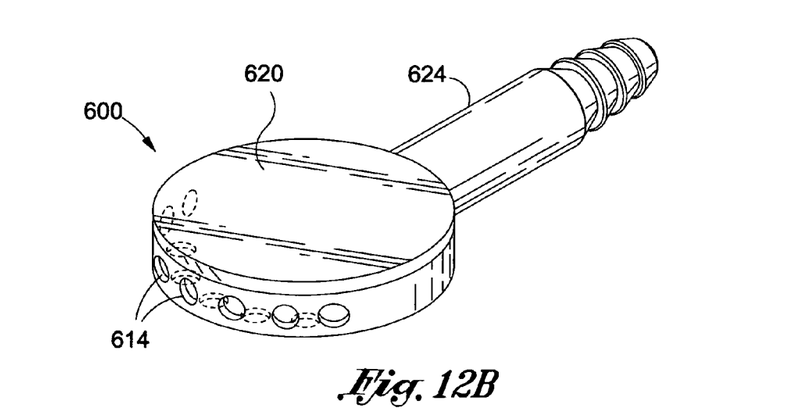
FIG. 12B is a top perspective view of FIG. 12A.
Figure 12C:
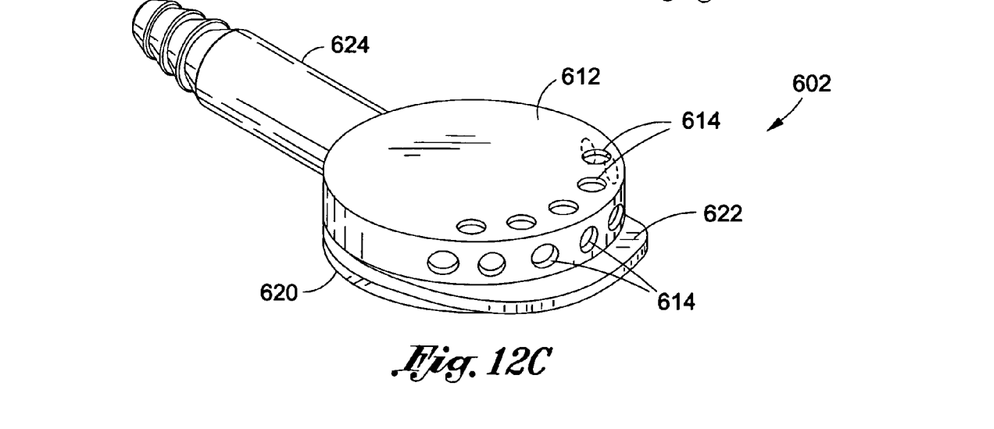
FIG. 12C is a bottom view similar to FIG. 12A but with extended edge.

Another modified version of the surgical suction tip apparatus 600 is shown in FIG. 12A-12C. The suction tip is very similar to FIG. 12 except the shape of the tip is rounded. This embodiment comprises a mirror 620 at the bottom wall surface and the rounded hollow cylindrical tip has a top wall 612 and outer side wall. There are pluralities of suction ports 614 formed in the top wall and the outer side wall. The cylindrical rounded housing is connected to a tube 624 for connection means to a vacuum tube or vacuum cannula with a handle. This embodiment may also have a protruded frontal edge or lip 622 as seen in FIG. 12C.

Figure 13:
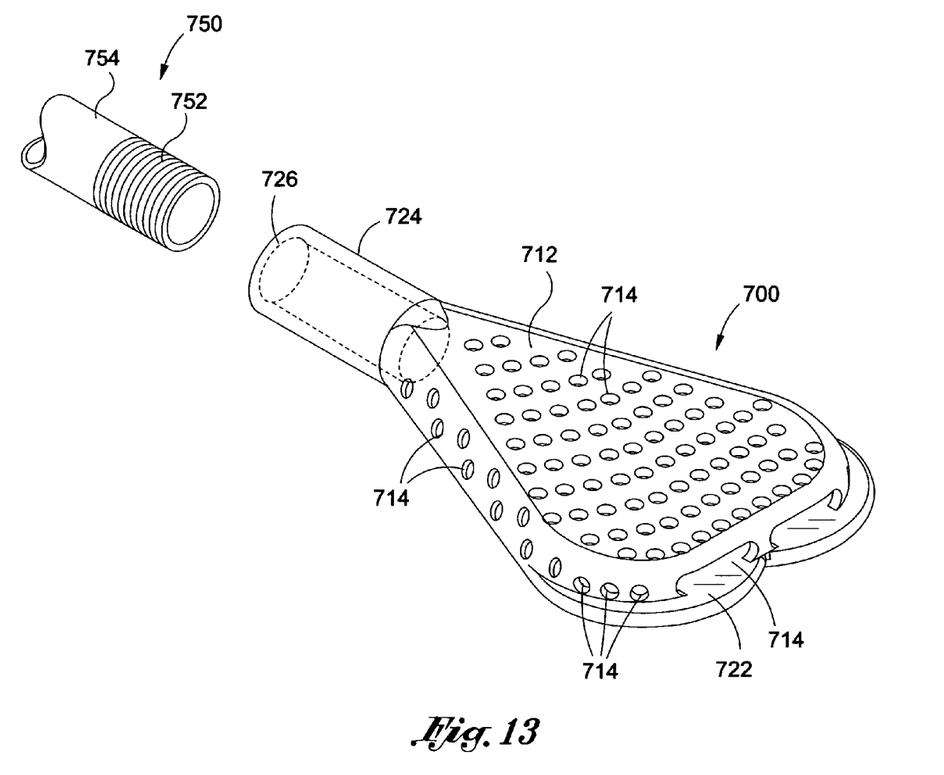
FIG. 13 is another modified version of the surgical suction tip shown in exploded view in conjunction with a detachable suction cannula.

FIG. 13 illustrate another modified suction tip 700 with groups of suction ports 714 formed in the top wall and on its sides. The intention of this design is to have more suction ports, in order to reduce the suction at its frontal tip and to divert the evacuation to the other area of the tip. Such tip is ideal for dentistry for purpose of fluid evacuation in the mouth as needed in some procedures such as upper & lower sealant procedure or molding cavities where the patient has excessive saliva.

The suction tip 700 connected to a tube 724 with internal thread 726. The suction tip 700 can easily connect to a suction cannula 750 with external thread 752 via the tube 724. Furthermore, the suction cannula body 754 can be connected to a vacuum source.

Figure 14:
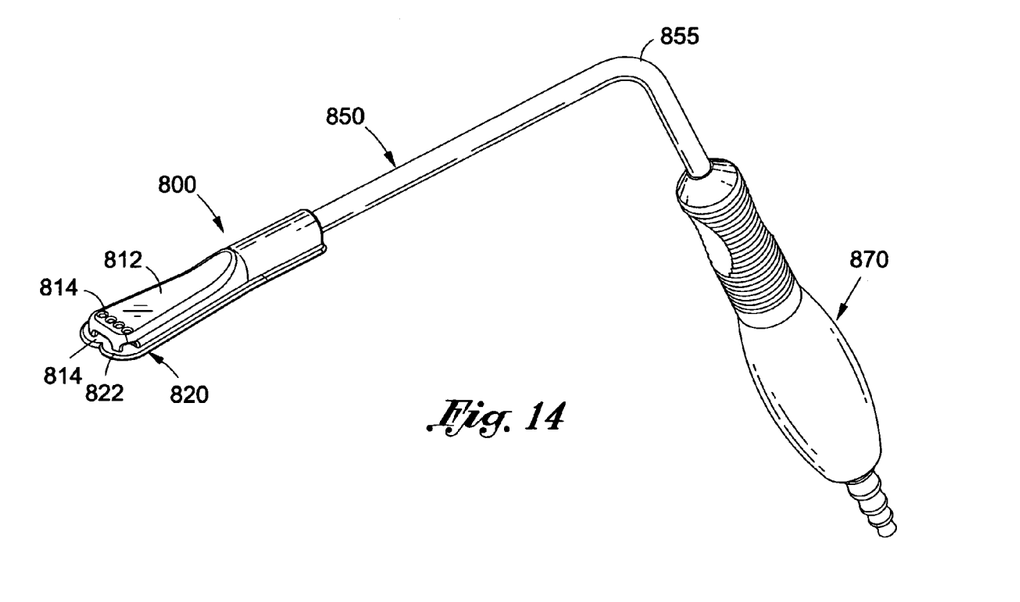
FIG. 14 is a perspective assembled view of surgical suction instrument with a suction tip with replaceable bottom portion.
Figure 15:
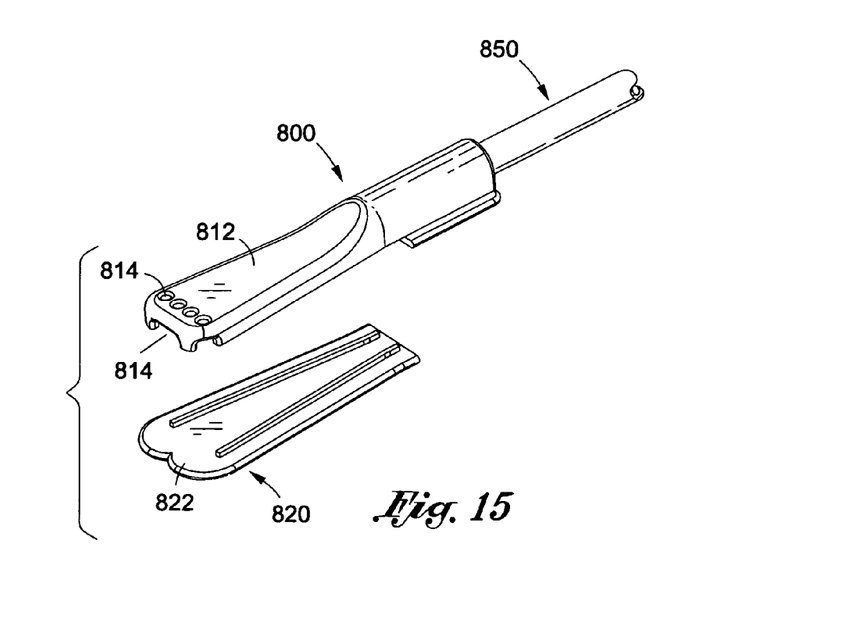
FIG. 15 is a exploded view of the suction tip shown in FIG. 14.
Figure 16:
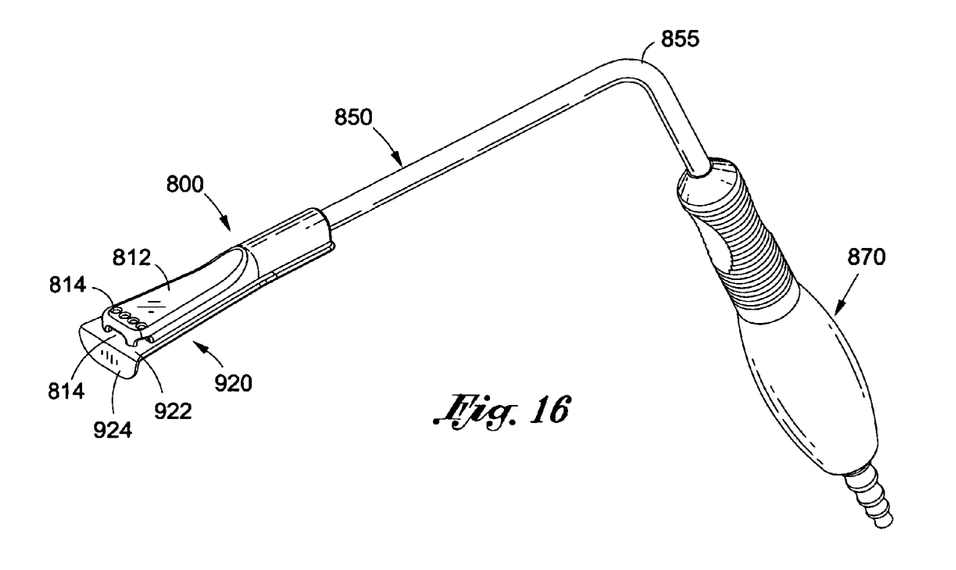
FIG. 16 is a perspective assembled view of surgical suction instrument with a suction tip with replaceable bottom portion with frontal bend of 90 degree.
Figure 17:
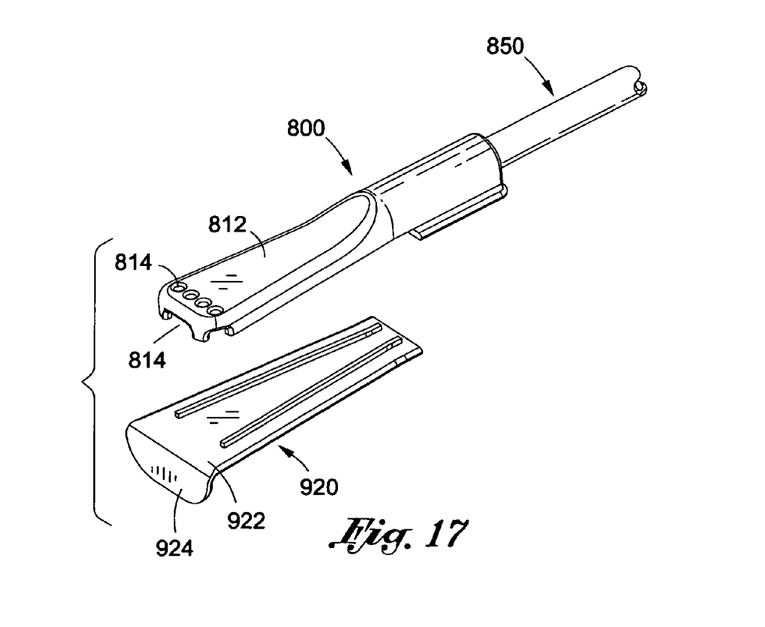
FIG. 17 is a exploded view of the suction tip shown in FIG. 16.
Figure 18:
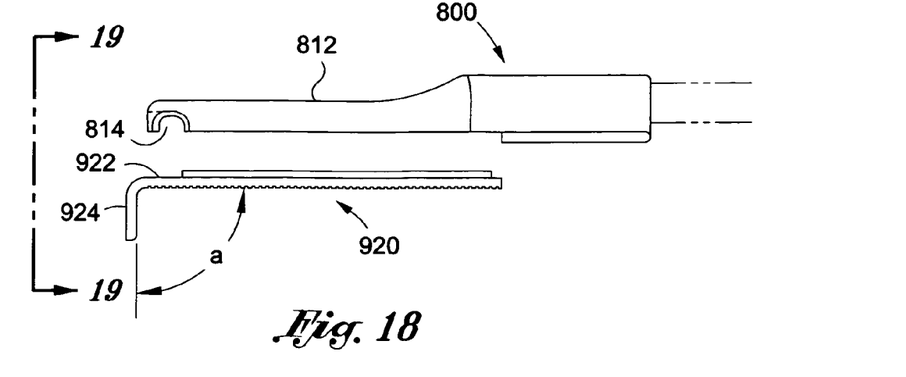
FIG. 18 is an exploded side view of suction tip shown in FIG. 17.
Figure 19:
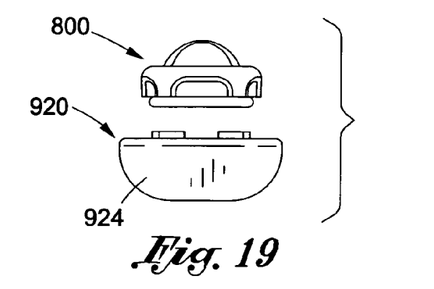
FIG. 19 is an exploded frontal view of FIG. 18.
Figure 20:
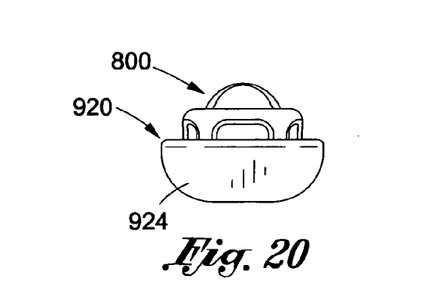
FIG. 20 is an assembled fontal view shown in FIG. 19.
Figure 21:
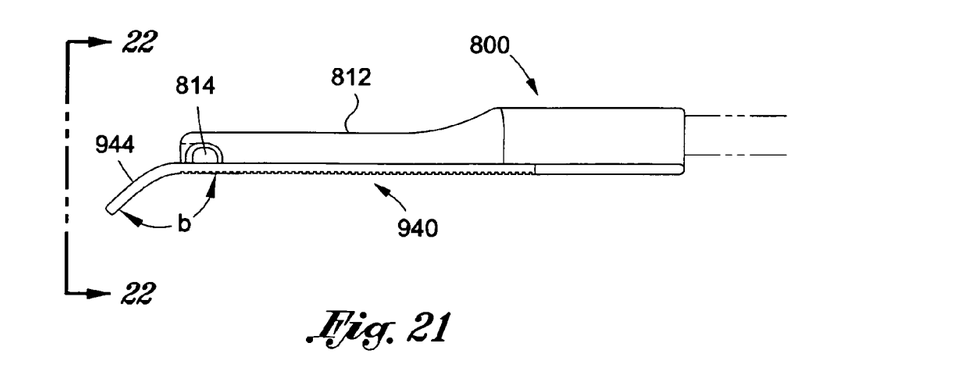
FIG. 21 is an assembled view of the suction tip with another version of bottom portion with 60 degrees frontal bend.
Figure 22:
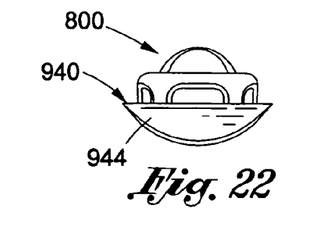
FIG. 22 is an assembled front view of as shown in FIG. 21 with around frontal bend portion.
Figure 23:
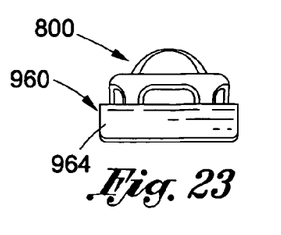
FIG. 23 is an assembled front view similar to FIG. 22, but the frontal bend portion is rectangular.
Figure 24:
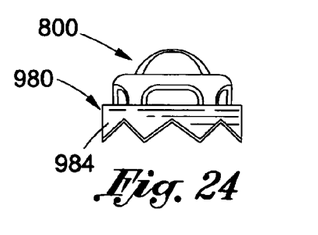
FIG. 24 is an assembled front view similar to FIG. 22, but the frontal bend portion is serrated.
Figure 25:
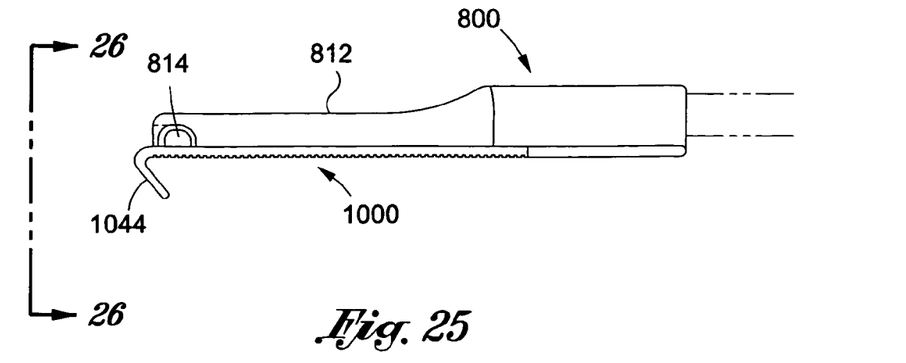
FIG. 25 is an assembled view of the suction tip with another version of bottom portion with 30 degrees frontal bend.
Figure 26:
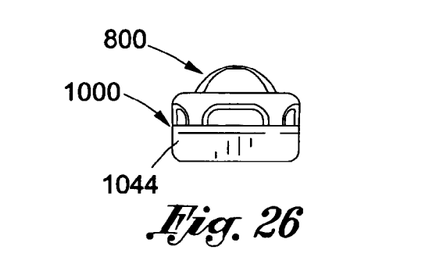
FIG. 26 is an assembled front view of as shown in FIG. 25.
Figure 27:
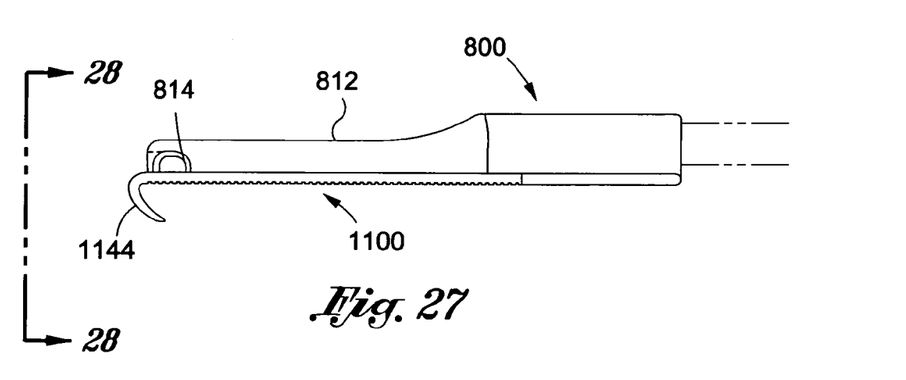
FIG. 27 is an assembled view of the suction tip with another version of bottom portion with 30 degrees frontal bend with fork designed shape.
Figure 28:
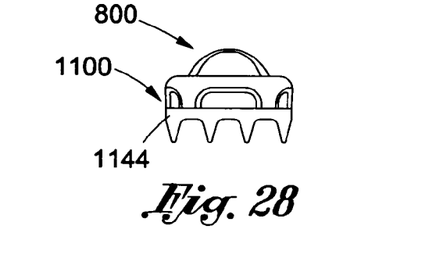
FIG. 28 is an assembled front view of as shown in FIG. 27.
Figure 29:
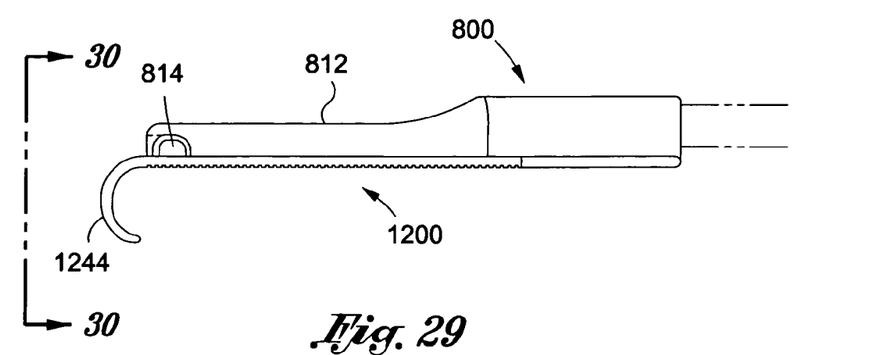
FIG. 29 is an assembled view of the suction tip with another version of bottom portion with curvature bend with fork designed shape.
Figure 30:
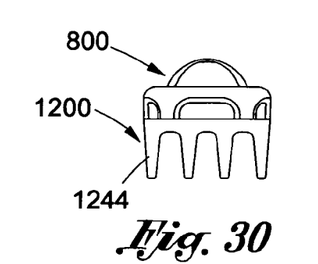
FIG. 30 is an assembled front view of as shown in FIG. 29.
Figure 31:
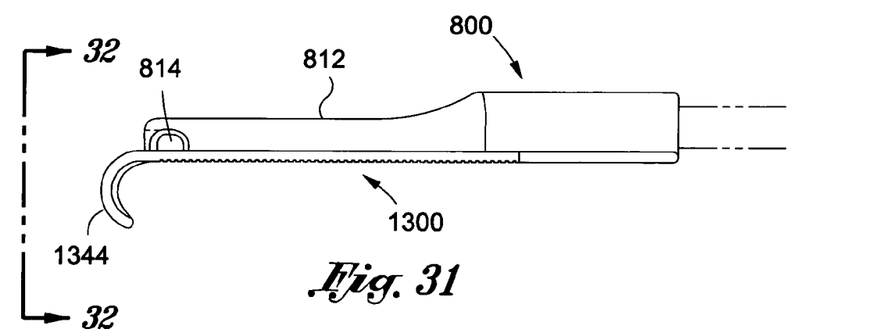
FIG. 31 is an assembled view of the suction tip with another version of bottom portion with curvature bend.
Figure 32:
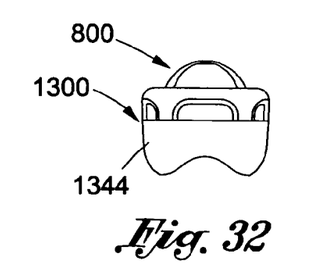
FIG. 32 is an assembled front view of as shown in FIG. 31.
Figures 33, 34:
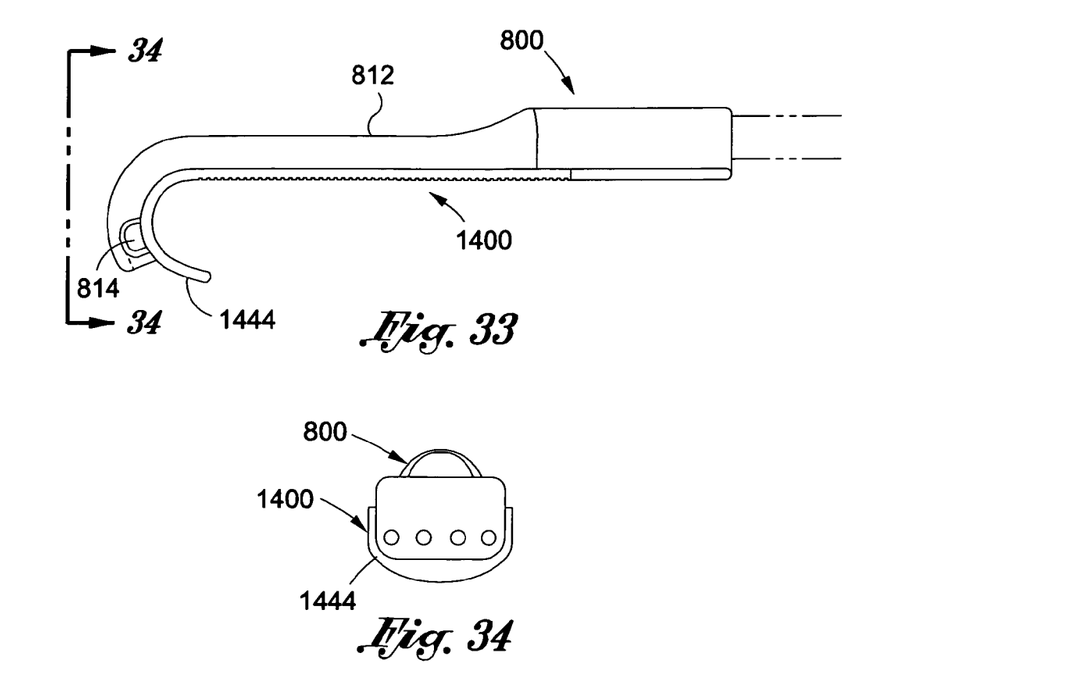
FIG. 33 is an assembled view of the suction tip with another version of bottom portion with more pronounced curvature bend.
FIG. 34 is an assembled front view of as shown in FIG. 33.
Figure 35:
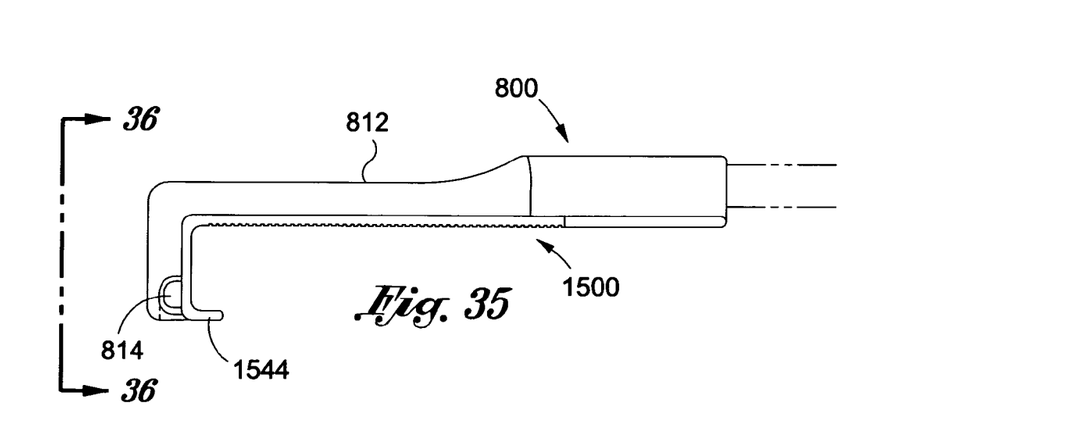
FIG. 35 is an assembled view of the suction tip with yet another version of bottom portion with more pronounced elbow bend.
Figure 36:
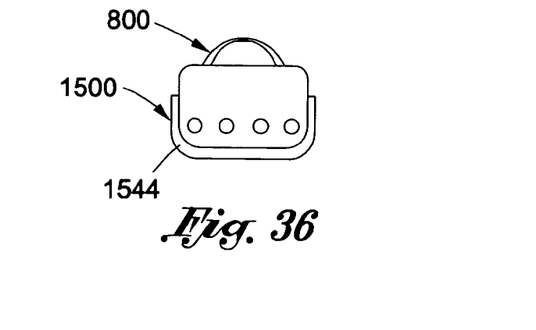
FIG. 36 is an assembled front view of as shown in FIG. 35.

FIG. 14 illustrate another modified suction tip 800 which is connected to a suction cannula 850 and a grip handle 870. The cannula 850 may have a elbow bend 855 with desired bend degrees such as 90° or 120°. This instrument may have additional optional features such as fiber optics and water spray at front of the tip portion. The suction tip 800 is comprising a top part 812 and bottom part 820. The bottom part can be welded or can be snapped into the top part. Therefore, it can be attachable or detachable if needed. The bottom part has a frontal edge 822 as shown in FIG. 15.

For some surgical procedures where the surgeon needs to retract tissue laterally, a bended front tip may be beneficial. FIG. 16-20 shows the modified suction tip 800 with bended tip. The bottom part 920 has a bended frontal edge 924 attached to the top part 812. The bend of the frontal portion may be designed in any degrees deflection such as 1 degree to 179 degrees with any desire shapes of the tip as shown in FIG. 21-36.

The front view of the bend tip can be rounded 944, rectangular 964 and/or serrated 984. The tip may also includes concavity or convexity shape as needed for specific surgical procedure. Furthermore, the tip may be bended inward 1044, 1144 as shown in FIG. 25-28. Or may have curvature bends 1244, 1344 or rounded corners as shown in 29-32.

The top part 812 can also be curved with respect to curvature bends 1444, 1544 as seen in FIG. 33-36. However, in order the suction tip to be effective when the suction is applied, the suction ports should be near the bended edge portion.

Figure 37:
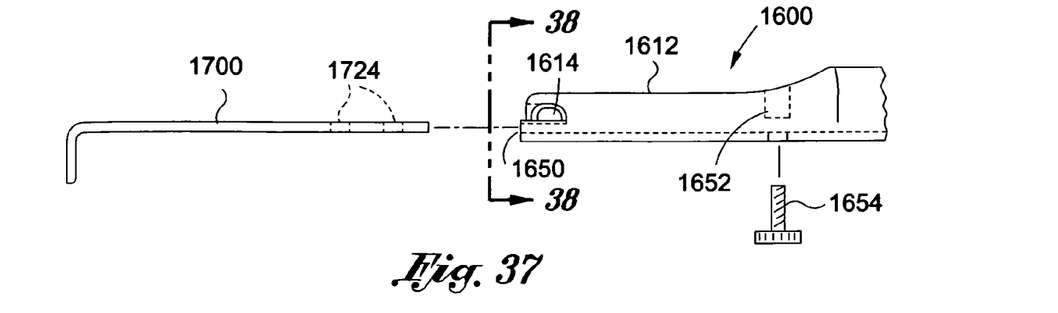
FIG. 37 is an exploded side view of alternative embodiment shown the replaceable bottom portion can be attached/detached respectfully.
Figures 38, 39:
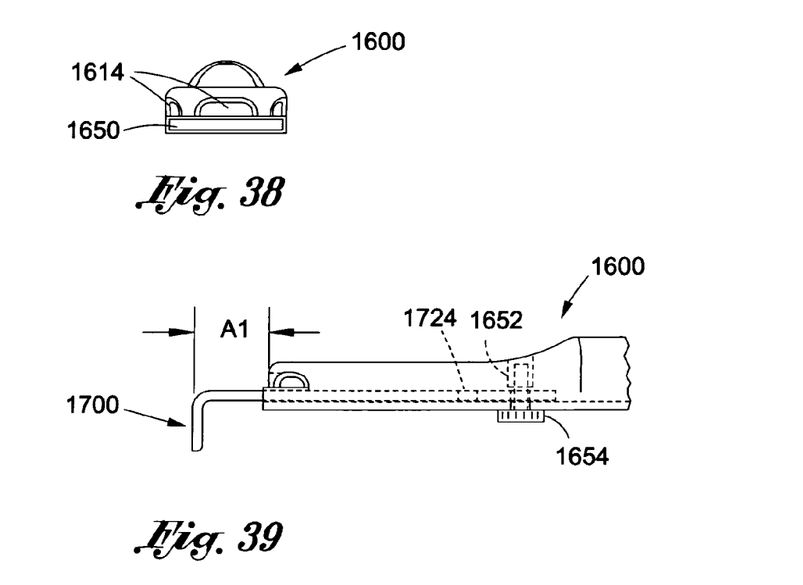
FIG. 38 is a planner view taken along line 38-38.
FIG. 39 is a similar view to FIG. 37, but the bottom portion is inserted into top portion of suction tip.

Another modified version of this embodiment is to be able to replaced the bended tip portion with another one in a quick release attachment/detachment. FIG. 37-38 are showing the suction tip main body 1600 with a pocket shaped 1650 that accommodate the bended tip portion 1700. Once the tip portion is inserted, the fastener 1654, 1652 secure the tip portion into the its positions.

Figure 40:
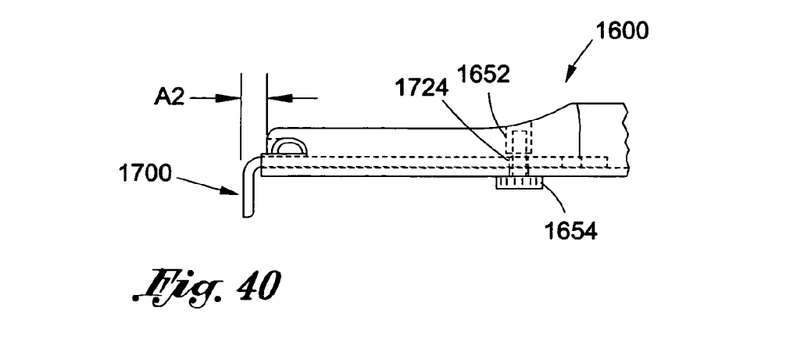
FIG. 40 is a similar view to FIG. 39, but the bottom portion is adjusted further into the top portion.

The tip portion may have several adjustment holes 1724 for adjusting into proper position with respect to main body 1600. As showing in FIG. 39-40, the adjustment length A1 and A2 showing two different positions for desire displacement with respect to suction ports for needed surgical procedures.

While this invention is susceptible of embodiments in many different forms, this specification and the accompanying drawings disclose only some specific forms as examples of the invention. The invention is not intended to be limited to the embodiments so described; however, the scope of invention is pointed out in the appended claims.

We claim:

1. A suction tip for a surgical instrument, comprising:
   a hollow housing having a top flat wall spaced apart from a bottom flat wall and including a tip chamber extending through the hollow housing between the top flat wall and the bottom flat wall, each one of the top flat wall and the bottom flat wall having a terminal end, the hollow housing including a proximal end and a distal end, the distal end having a widened tip portion that is wider than the proximal end;
   a ledge portion of the bottom flat wall extending outwardly past the terminal end of the top flat wall, wherein the ledge portion protrudes and is bended downwardly;
   a plurality of suction ports formed in the distal end and passing into the tip chamber, at least one of the suction ports being located proximate a terminal end of the top flat wall such that the suction port is set back from a terminal end of the ledge portion;
   an exit port located at the proximal end for discharging flow.

2. The suction tip according to claim 1, wherein the protruded ledge portion is bended downwardly has a range of possible bends from 1 degree to 179 degrees.

3. The suction tip according to claim 1, wherein the protruded ledge portion is bended downwardly has a range of possible rounded bends.

4. The suction tip according to claim 1, wherein the protruded ledge portion of the bottom flat wall can be detachable/attachable to the top flat wall.

5. The suction tip according to claim 1, wherein the protruded ledge portion is bended, the bend has a rounded tip.

6. The suction tip according to claim 1, wherein the protruded ledge portion is bended, the bend has a rectangular tip.

7. The suction tip according to claim 1, wherein the protruded ledge portion is bended, the bend has a serrated tip.

8. The suction tip according to claim 1, wherein the protruded ledge portion is bended, the bend has a fork type tip.

9. The suction tip according to claim 1, wherein the protruded ledge portion is bended, the bend has a concave tip.

10. The suction tip according to claim 1, wherein the protruded ledge portion is bended, the bend has a convex tip.

* * * * *